US00PP32333P2

(12) United States Plant Patent
Jimenez

(10) Patent No.: US PP32,333 P2
(45) Date of Patent: Oct. 13, 2020

(54) ***SANSEVIERIA* PLANT NAMED 'SPEARMINT'**

(50) Latin Name: *Sansevieria trifasciata*
Varietal Denomination: Spearmint

(71) Applicant: FLORICA FARMS, INC., Eustis, FL (US)

(72) Inventor: Francisco Emiliano Corrales Jimenez, Alajuela (CR)

(73) Assignee: FLORICA FARMS, INC., Eustis, FL (US)

( * ) Notice: Subject to any disclaimer, the term of this patent is extended or adjusted under 35 U.S.C. 154(b) by 0 days.

(21) Appl. No.: 16/501,642

(22) Filed: May 17, 2019

(51) Int. Cl.
*A01H 5/02* (2018.01)
*A01H 6/12* (2018.01)

(52) U.S. Cl.
USPC ..... Plt./382
CPC ..... *A01H 6/12* (2018.05)

(58) Field of Classification Search
USPC ..... Plt./382
CPC ..... A01H 6/12
See application file for complete search history.

*Primary Examiner* — Anne Marie Grunberg
(74) *Attorney, Agent, or Firm* — Foley & Lardner LLP

(57) ABSTRACT

The new variety 'Spearmint' is a type of "long leaves *Sansevieria*" plant. It can reach 80 cm in length, with an average of approximately 3-5 leaves per plant. The plant is cylindrically shaped, the arrangement of the leaves is in the form of a rosette. The leaf blade is greyed-green colored, with dark green colored non-uniform horizontal variegated bands in both sides of the leaves, and green margins. Shows colors very different from its parent variety 'Wintergreen' (Patented, U.S. Plant Pat. No. 24,939), and 'Bantel Sensation' (unpatented). Unlike its parent variety it shows variegated leaves (different green tones on the irregular bands) and 'Spearmint' also presents less leaves per rosette.

3 Drawing Sheets

Figure 1:
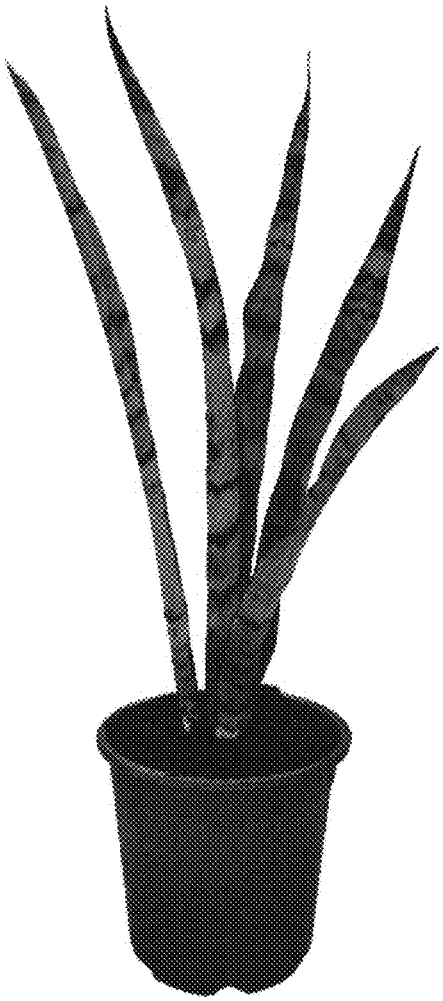

Latin name of the genus and species of the claimed plant: *Sansevieria trifasciata.*

Variety denomination: SPEARMINT.

BACKGROUND OF THE INVENTION

The present invention relates to a new and distinct cultivar of *Sansevieria* plant, botanically known as *Sansevieria trifasciata*, of the family Ruscaceae hereinafter referred to by the cultivar name 'Spearmint'.

*Sansevieria* is a monocotyledonous flowering plant which can be produced in either hard-leafed or soft-leafed varieties for interior use as a house plant or outdoors. *Sansevieria* is a monocotyledonous and succulent, flowering plant which can be produced in either hard-leafed or soft-leafed varieties for interior use as a house plant or outdoors ornamental plant.

The new variety 'Spearmint' originated from a naturally-occurring mutation of the *Sansevieria trisfasciata* variety 'Wintergreen' (patented, U.S. Plant Pat. No. 24,939). The new *Sanseviera* 'Spearmint' was discovered and selected by the inventor Francisco Emiliano Corrales Jiménez, as a single sprouting rare mutated plant in a 'Wintergreen' plantation, a controlled environment, in 2017 in Guatuso, San Carlos, Alajuela province, Costa Rica.

Asexual reproduction of the new *Sansevieria* cultivar by vegetative cuttings was first performed in 2017 in Guatuso, San Carlos, Alajuela, and demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'Spearmint', which in combination distinguish this *Sansevieria* as a new and distinct cultivar:

1. Variegated foliage with different green tones on the irregular bands, and dark green colored margin bands in the leaf blade
2. wide and lanceolate leaves, supported in a rosette.
3. 50-80 cm plant height.
4. Plant habit: Erect
5. Needs little water and is very drought tolerant.

The new variety 'Spearmint' is considered a variety of *Sansevieria* in the group denominated as "long leaves *Sansevieria* varieties". The new variety presents an average of 3-5 leaves per plant when it reaches its maturity (between 8-12 months). The new variety has an erect growth habit and the entire plant can reach a height range between 50-80 cm. The leaves are narrow (3-5 cm average measured at the widest part of the mature leaf) and lanceolate, with a soft waxy texture. The blades are thin and slightly wavy. The plant has a cylindrical shape.

The new variety is very drought tolerant, adapts to conditions of light and shade (interior and exterior), and shows high tolerance level to Anthrachnose (*Colletotrichum sansvierae*) disease.

The leaf blade is greyed-green colored (RHS 138D), with non-uniform horizontal variegated bands in both sides of the leaves dark green (RHS 141A) colored, and green margins (RHS 141A).

The leaf blade is green colored (RHS 133D), with non-uniform horizontal variegated bands in both sides of the leaves, dark green (RHS 133A) colored.

The variety 'Wintergreen' gave rise to the variety 'Spearmint'. The 'Spearmint' is also considered part of the "long leaves varieties" group. The claimed variety shows little less vigor than 'Wintergreen', has a low number of leaves per plant (3-5), with an average width of 3-5 cm (measured in the middle of the mature leaf) The growth habit is erect and presents narrow leaves supported in a rosette. The entire plant can reach a size between 50-80 cm. The plant has, a cylindrical shape.

Plants of the new *Sansevieria* 'Spearmint' differ from plants of the parental cultivar, 'Wintergreen' (patented) in the characteristics described in Table 1.

TABLE 1

Comparison between new cultivar 'Spearmint' and its parent variety 'Wintergreen'.

| Characteristic | New Cultivar 'Spearmint' | Parent 'Wintergreen' (patented) |
|---|---|---|
| Plant Vigor | less vigorous (less leaves) | more vigorous (more leaves) |
| Color | variegated green leaves, greyed-green leaves with irregular thin dark green horizontal bands and green margins | variegated leaves (light yellowish green cross-banding and green margins) |
| Shape | Narrow and lanceolated leaves on a rosette | Narrow and lanceolated leaves on a rosette |
| Texture of leaves | smooth-textured leaves | smooth-textured leaves |

Of the many commercial cultivars known to the present inventor, the most similar in comparison to the new *Sansevieria* 'Spearmint' is the *Sansevieria* 'Wintergreen'.

Plants of the new variety 'Spearmint' can also be compared to the commercial variety *Sansevieria* 'Bantel Sensation', unpatented. Plants of the new variety differ in the following characteristics:

1. Foliage of the new variety is wider, averaging 5.0 cm, compared to foliage of 3 cm in width of the comparator.
2. Color of the new variety has irregular horizontal bands with different dark green tones, compared to the longitudinal bands with very pale green tones of the comparator.
3. Foliage of the new variety has a less acute apex than that of the comparator.

BRIEF DESCRIPTION OF THE PHOTOGRAPHS

The accompanying photographs illustrate the overall appearance of the new *Sansevieria* cultivar 'Spearmint' showing the colors as true as is reasonably possible with colored reproductions of this type. Colors in the photographs may differ slightly from the color value cited in the detailed botanical description which accurately describe the color of 'Spearmint'.

FIG. 1—Shows a side view of an eight-month old plant of *Sansevieria* 'Spearmint' in a 21 cm diameter pot.

Figure 2:
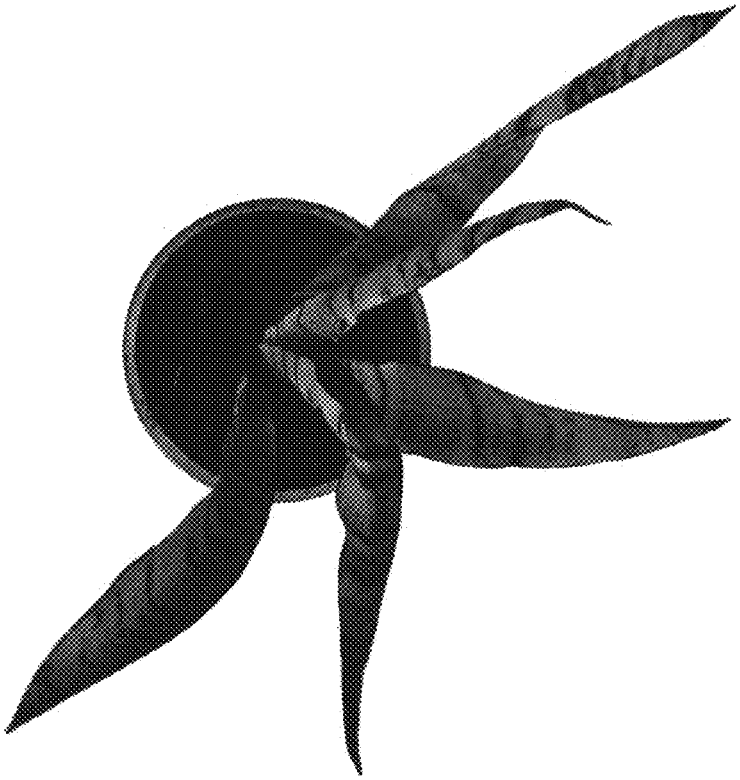

FIG. 2—Shows a top down view of a typical eight-month old plant of *Sansevieria* 'Spearmint'.

Figure 3:
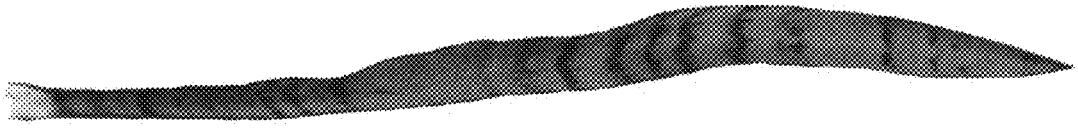
Figure 3:
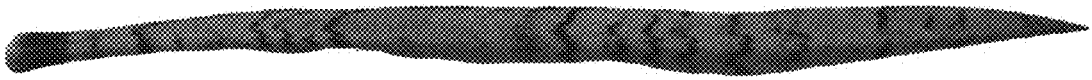

FIG. 3—shows a close-up view of the typical leaves of 'Spearmint' from an eight-month old plant (upper side—A, under side—B).

DETAILED BOTANICAL DESCRIPTION

The new *Sansevieria* 'Spearmint' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Sansevieria* cultivar 'Spearmint' as grown in open-field conditions at Guatuso, San Carlos, Alajuela province, Costa Rica, under conditions which closely approximate those generally used in commercial practice. 28° C. during the day and 18° C. at night. Plants grow under natural light conditions. This crop does not require constant fertilization, to increase production per area about 200 kg ha−1 N, 150 kg ha−1 of P and 100 kg ha−1 K are required, the production is closely related with soil conditions in which they are grown.

Color references are made to The Royal Horticultural Society Colour Chart (R.H.S. online, March 2019), except where general colors of ordinary significance are used. The photographs and descriptions were taken during the dry season in Guatuso, San Carlos, Alajuela province, Costa Rica when outdoor day temperature was 28° C. The age of the plants described is 8 months.

Classification:

*Botanical.*—*Sansevieria trifasciata.*

*Variety denomination.*—Spearmint.

Parentage: *Sansevieria trifasciata* 'Wintergreen' (U.S. Plant Pat. No. 24,939).

Optimal growth conditions:

*Light intensities.*—High adaptability to outdoor or indoor conditions.

*Temperature.*—Day: 24° C. to 35° C. Night: 18° C. to 23° C.

*Temperature tolerance.*—Tolerant to temperatures between 18° C. and 35° C.

*Fertilization.*—200, 150 and 100 kg $ha^{-1}$ of N, P and K.

*Growth regulators.*—Not necessary.

Propagation:

*Type.*—Vegetative, by rooted cuttings.

*Rooting habit description.*—Rhizomes, with short roots.

*Time to initiate roots.*—15 to 22 days at 20-25° C.

*Faster time to produce a rooted cutting.*—About 60 to 90 days at 20-25° C.

Plant:

*General appearance and form.*—

*Height.*—About 80 cm when grown in ground; about 60 cm when grown in a 21 cm size container.

*Spread.*—About 15 cm when grown in ground; About 10 cm when grown in 21 cm size container.

*Form.*—Monocot; leaf bases arranged in a rosette around growth point.

*Shape.*—Cylindrical.

*Growth rate and habit.*—About 2.5 cm per week; upright.

*Fragrance.*—None.

*Stem.*—Modified (Rhizome and foliage). Length: About 12 cm when grown in ground; About 8 cm when grown in 21cm size container. Diameter: About 1.8-2.0 cm. Shape: round. Texture: rough. Color: RHS 17A. Strength: strong and durable. Internode length: About 0.5 mm to 0.7 mm.

Foliage:

*Quantity*.—About 3-5 leaves.

*Arrangement and attachment*.—Single, alternate; leaf bases arranged in a rosette around growth point.

*Leaf length*.—About 60 cm.

*Leaf width*.—About 3-5 cm.

*Overall shape of leaf*.—Lanceolated.

*Apex shape*.—Acute, triangular.

*Base shape*.—Plane.

*Margin*.—Sharp, smooth.

*Texture*.—Upper Surface: smooth and waxy texture. Under Surface: smooth and waxy texture.

*Pubescence*.—None.

*Color of mature leaf*.—Upper Surface: Green gray leaves RHS138D, with non-uniform thin horizontal dark green bands RHS141A and green margins RHS141A. Lower Surface: Green gray leaves RHS138D, with non-uniform thin horizontal dark green bands RHS141A and green margins RHS141A.

*Color of immature leaf*.—Upper Surface: Green gray leaves RHS138D, with non-uniform thin horizontal dark green bands RHS141A and green margins RHS141A. Lower Surface: Green gray leaves RHS138D, with irregular thin dark green crossbanding RHS141A and green margins RHS141A.

*Venation*.—Pattern: longitudinal/parallel leaf shape. Color: none. Leaf fragrance: None.

Inflorescence description:

*Arrangement and type*.—Inflorescence.

*Orientation at opening*.—Out of the spike.

*Quantity*.—Per Plant with at least one open flower: About 20 at 2 weeks.

*Inflorescence size*.—Length: About 30 cm. Diameter: About 0.4 cm.

*Flower size*.—Length: About 2 cm. Diameter: About 0.5 cm. Depth: About 1 cm.

*Fragrance*.—None.

*Bud*.—

*Rate of opening*.—About 7 to 8 days, according to weather.

*Shape*.—Ovoid.

*Length*.—About 3 cm.

*Diameter*.—About 1 cm.

*Color*.—Apex: RHS 149 B. Base: RHS 142 B.

*Texture* (*both surfaces*).—Smooth.

Petals:

*Quantity*.—6.

*Arrangement*.—Star-shaped.

Reproductive organs:

*Androecium*.—Stamen: Number: 6 per flower. Length: About 1.2 cm. Color: RHS 149B. Anther: Length: About 2 mm. Width: About 1 mm. Color: RHS 149B. Filament: Length: About 1.3 cm. Color: RHS 149B. Pollen: Amount: moderate. Color: RHS 149B.

*Gynoecium*.—Pistil: Number: One per flower. Length: About 2.0 cm. Stigma: Length: About 0.6 mm. Width: About 1 mm. Color: RHS 149B. Style: Length: About 2.2 cm. Color: RHS 149B. Ovary: Length: About 4 mm. Width: About 2 mm. Color: RHS 149B.

Weather resistance: Drought tolerant.

Disease/pest resistance: High tolerance to Anthrachnose (*Colletotrichum sansevieria*).

Disease/pest susceptibility: not observed so far.

I claim:

1. A new and distinct *Sansevieria* plant named 'Spearmint', substantially as illustrated and described herein.

* * * * *

A

B